(12) United States Patent
Dejonghe et al.

(10) Patent No.: US 7,863,469 B2
(45) Date of Patent: Jan. 4, 2011

(54) CHEMICAL PROCESS FOR PREPARATION OF INTERMEDIATES

(75) Inventors: Jean-Paul Dejonghe, Louvain-la-Neuve (BE); Koen Peeters, Wetteren (BE); Marc Renard, Louvain-la-Neuve (BE)

(73) Assignee: AstraZeneca AB, Sodertalje (SE)

( * ) Notice: Subject to any disclaimer, the term of this patent is extended or adjusted under 35 U.S.C. 154(b) by 155 days.

(21) Appl. No.: 11/833,263

(22) Filed: Aug. 3, 2007

(65) Prior Publication Data

US 2008/0132719 A1   Jun. 5, 2008

(30) Foreign Application Priority Data

Aug. 5, 2006   (GB) ................. 0615619.4

(51) Int. Cl.
*C07D 303/08*   (2006.01)
(52) U.S. Cl. .................................. 549/563
(58) Field of Classification Search ............ 549/563
See application file for complete search history.

(56) References Cited

U.S. PATENT DOCUMENTS

| 4,411,925 | A | | 10/1983 | Brennan et al. |
| 4,590,292 | A | | 5/1986 | Blackwell et al. |
| 4,933,477 | A | * | 6/1990 | Goetz et al. ............ 549/519 |
| 5,225,602 | A | * | 7/1993 | Hoelderich et al. ......... 568/41 |
| 6,552,217 | B2 | | 4/2003 | Hubbs et al. |
| 6,683,216 | B1 | | 1/2004 | Zoeller et al. |
| 2008/0071114 | A1 | * | 3/2008 | Mitsuda et al. ........... 564/414 |

FOREIGN PATENT DOCUMENTS

| DE | 3909142 | 10/1990 |
| DE | 4315623 | 11/1994 |
| DE | 19523868 | 1/1997 |

| WO | 0192263 | 12/2001 |

OTHER PUBLICATIONS

Tomoskozi, Tetrahedron (1963), 19(12), 1969-1979, Abstract.*
Armstrong et al., "Stereocontrolled synthesis of 3-(trans-2-aminocyclopropyl)alanine, a key component of belactosin A," Organic Letters (2003) 5(13):2331-2334.
Barbieri et al., "Chemo-enzymatic synthesis of (R)-and (S)-3,4-dichlorophenylbutanolide intermediate in the synthesis of sertraline," Tetrahedron: Asymmetry (1999) 10:3931-3937.
Singh et al., "Development of a practical, safe, and high-yielding process for the preparation of enantiomerically pure trans-cyclopropane carboxylic acid," Organic Process Research & Development (2002) 6:618-620.
Office Action dated Mar. 20, 2009 received in copending U.S. Appl. No. 11/833,266.
Engel et al., J Org Chem (1988) 53(20):4748-4758.
Database CAPLUS on STN, Acc. No. 1971:435269, Filler et al., ",", J Chem Soc, Section C: Organic (1971) 11:2062-2068 (abstract).
Yasui et al., J Am Chem Soc (1987) 109(8):2311-2320.
Wang et al., "Enantioselective synthesis of chiral cyclopropane compounds through microbial transformations of trans-2-arylcyclopropanecarbonitriles," Tetrahedron Letters (2000) 41:6501-6505.
White "New reactions of polyfluoroaromatic compounds. Part II. Polyfluoroaralkyl amines," J. Chem Soc. (1971) 2062-2068.
Notice of copending applications.
Office Action dated Oct. 23, 2009 received in copending U.S. Appl. No. 11/833,266.
Notice of allowance dated May 6, 2010 received in copending U.S. Appl. No. 11/833,266.

* cited by examiner

*Primary Examiner*—Janet L Andres
*Assistant Examiner*—David E Gallis
(74) *Attorney, Agent, or Firm*—Pepper Hamilton LLP

(57) ABSTRACT

The present invention relates to compounds useful as pharmaceutical intermediates, to processes for preparing the intermediates, to intermediates used in the processes, and to the use of the intermediates in the preparation of pharmaceuticals. In particular, the present invention concerns enantiomerically pure trans-cyclopropane carboxylic acid derivatives, processes for preparing the carboxylic acid derivatives and their use in preparing pharmaceuticals.

17 Claims, No Drawings

CHEMICAL PROCESS FOR PREPARATION OF INTERMEDIATES

CROSS-REFERENCE TO RELATED APPLICATIONS

This application claims priority to Great Britain Application No. 0615619.4 filed Aug. 5, 2006, which is incorporated herein by reference in its entirety.

FIELD OF THE INVENTION

The present invention relates to compounds useful as pharmaceutical intermediates, to processes for preparing the intermediates, to intermediates used in the processes, and to the use of the intermediates in the preparation of pharmaceuticals. In particular, the present invention concerns enantiomerically pure trans-cyclopropane carboxylic acid derivatives, processes for preparing the carboxylic acid derivatives and their use in preparing pharmaceuticals.

BACKGROUND OF THE INVENTION

The compound [1S-(1α,2α,3β(1S*,2R*),5β)]-3-[7-[2-(3,4-difluorophenyl)-cyclopropyl]amino]-5-(propylthio)-3H-1,2,3-triazolo[4,5-d]pyrimidin-3-yl]-5-(2-hydroxyethoxy)-cyclopentane-1,2-diol (Compound A), and similar such compounds, are disclosed in WO 00/34283 and WO 99/05143. These compounds are disclosed as $P_{2T}$ (which is now usually referred to as $P_2Y_{12}$) receptor antagonists. Such antagonists can be used as, inter alia, inhibitors of platelet activation, aggregation or degranulation.

We have now found an advantageous process for preparing enantiomerically pure trans-cyclopropane carboxylic acid derivatives which may be used in the preparation of Compound A. The process offers advantages such as, for example: diastereoselecivity, enantioselectivity, high yield, potential for manufacturing (e.g. reagents and procedures suitable for large scale production, non-hazardous reagents, less waste).

SUMMARY OF THE INVENTION

The present invention provides processes for preparing a compound of formula IV

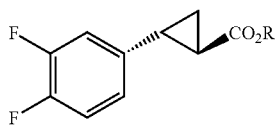

(IV)

wherein R is an alkyl group, comprising: treating a compound of formula III

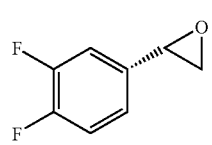

(III)

with a compound of formula 3

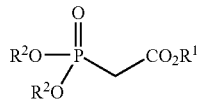

(3)

wherein $R^1$ and $R^2$ are, independently, alkyl.

The present invention also provides processes for preparing a compound of formula IV

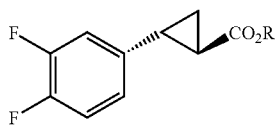

(IV)

wherein R is an alkyl group, comprising: a) reducing a compound of formula I (I)

to give a compound of formula II (II)

b) treating the compound of formula II with a base to give a compound of formula III (III)

and c) treating the compound of formula III with a compound of formula 3

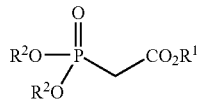

(3)

wherein $R^1$ and $R^2$ are, independently, selected from alkyl.

The present invention also provides processes for preparing a compound of formula IV

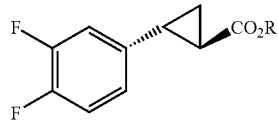
(IV)

wherein R is an alkyl group, comprising: a) treating the compound of formula II

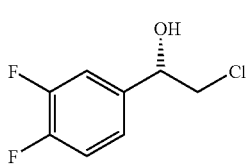
(II)

with a base; and b) treating the product of a) with a compound of formula 3

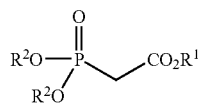
(3)

wherein $R^1$ and $R^2$ are, independently, selected from alkyl.

The present invention also provides processes for preparing a compound of formula VII

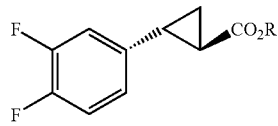
(VII)

comprising treating the compound of formula IV

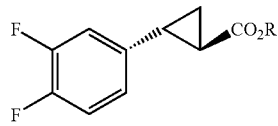
(IV)

with ammonia in the presence of a suitable base.

The present invention also provides a compound of formula II

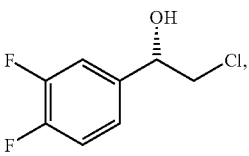
(II)

or formula III

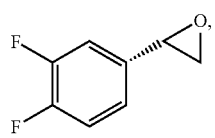
(III)

or formula VII

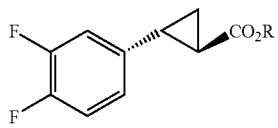
(VII)

DESCRIPTION OF EMBODIMENTS

According to a first aspect of the present invention there is provided one or more compounds of formula IV

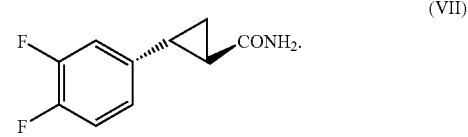
(IV)

wherein R is an alkyl group.

For any of the embodiments described herein, suitable values of R include, but are not limited to, for example, $(C_{1-16})$alkyl, such as methyl, ethyl, n-propyl, iso-propyl, n-butyl, and tert-butyl. In some embodiments, R is ethyl.

The compound of formula IV may be prepared from a compound of formula II

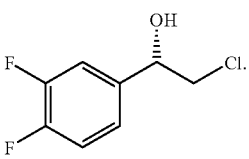
(II)

According to a further aspect of the present invention there is provided processes for preparing one or more compounds of formula II from a compound of formula I.

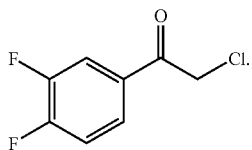
(I)

The compound of formula I is reduced to the compound of formula II. The reduction is carried out using a suitable reducing agent. Suitable reducing agents will include those which are able to reduce the carbonyl group in the compound of formula I to the hydroxyl group of formula II and give an enantiometric excess of the compound of formula II with the stereo chemistry shown in formula II. Examples of suitable conditions include, for example, catalytic reduction or use of a transition metal with chiral ligand.

A particular example of a suitable reducing agent is oxazaborolidine which may be formed by mixing trimethoxy borane and S-diphenylprolinol, followed by addition of borane dimethylsulphide. This is generally carried out in an inert solvent such as toluene. The temperature is conveniently maintained at a temperature in the range 25 to 45° C., for example 35 to 40° C.

The compound of formula I is treated with the reducing agent so formed. This is generally carried out in an inert solvent such as toluene. The temperature is conveniently maintained at a temperature in the range 25 to 45° C., for example 35 to 40° C.

A compound of formula IV may be prepared by treating a compound of formula III

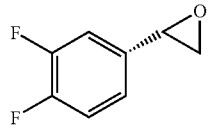
III with a compound of formula 3

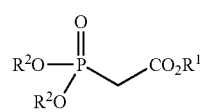
(3)

wherein $R^1$ and $R^2$ are, independently, selected from alkyl such as $(C_{1-6})$alkyl. A suitable compound of formula 3 is triethyl phosphonoacetate.

The reaction is generally carried out in an inert solvent such as toluene. The reaction is generally carried out at a temperature in the range 30 to 80° C., conveniently 40 to 60° C., e.g. 40° C. The reaction may conveniently be carried out in the presence of a base. Examples of suitable bases include, but are not limited to, sodium hydride and alkali metal (for example potassium or sodium) alkoxides (for example t-butoxide). Specific examples are potassium and sodium t-butoxide.

The compound of formula III may be prepared by treating the compound of formula II with a base, such as an alkali metal hydroxide, for example sodium hydroxide. This is conveniently carried out in a suitable solvent such as water.

The compound of formula II may be converted to a compound of formula IV via the compound of formula III,

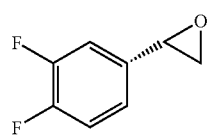
III without isolation of the compound of formula III.

In a particular embodiment of the present invention, the compound of formula II is converted to a compound of formula IV by treating the compound of formula II with a base, such as sodium hydride. This is generally carried out in an inert solvent such as toluene. This is treated with triethyl phosphonoacetate. This is generally carried out at a temperature in the range 30 to 80° C., conveniently 40 to 60° C., e.g. 40° C.

The present invention also provides processes for preparing a compound of formula VII

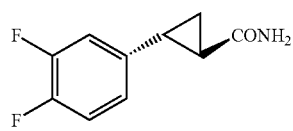
VII which comprises treating a compound of formula IV with ammonia in the presence of a suitable base. Suitable bases include, but are not limited to, alkali metal alkoxides such as potassium methoxide or sodium methoxide. An agent such as methyl formiate may also be present. The reaction is generally carried out in a suitable solvent such as an alcohol in a suitable solvent. In one embodiment, the reaction is carried out in toluene and methanol.

A compound of formula IV may be treated with the base and then treated with ammonia. Preferably, the reaction is under pressure during the treatment with ammonia. An example of a suitable pressure is 2 to 10 bar. The reaction may be carried out at an elevated temperature, such as 40 to 70° C., for example at about 60° C.

The present invention is also directed to compounds of formula IV and VII.

The present invention also provides novel intermediates of formula II, III, or VII.

Any of the embodiments described herein can be combined with any of the other embodiments described herein.

In order that the invention disclosed herein may be more efficiently understood, examples are provided below. It should be understood that these examples are for illustrative purposes only and are not to be construed as limiting the invention in any manner.

EXAMPLES

Example 1

Preparation of 2-chloro-1-(3,4-difluorophenyl)ethanone

Aluminium trichloride (210.2 g) was added to 1,2-difluorobenzene (200.0 g) at room temperature. The obtained slurry was heated to 50° C., then chloroacetyl chloride (198.0 g) was added over 50 minutes. The reaction mixture was stirred for an additional 60 minutes, then added slowly to a mixture of ice (786.0 g), water (196.0 g) and 37 wt % hydrochloric acid (297.0 g), during the addition the temperature was kept below 60° C. After the addition, the reaction mixture was heated to 60° C. and the layers separated. The organic layer was washed twice with a 20 w/v % sodium chloride solution (200.0 mL). 2-Chloro-1-(3,4-difluorophenyl)ethanone (270.2 g) was obtained by vacuum distillation of the organic layer.

Spectral data:

$^1$H-NMR of 2-chloro-1-(3,4-difluorophenyl)ethanone in CDCl$_3$, 300 mHz

| δ (ppm) | H | Pattern |
|---|---|---|
| 4.7 | ClCH$_2$ | S |
| 7.3 | Ph H-5 | d × d × d × d |
| 7.8 | Ph H-6 | M |
|  | Ph H-2 |  |

$^{13}$C-NMR of 2-chloro-1-(3,4-difluorophenyl)ethanone in CDCl$_3$, 75 MHz

| δ (ppm) | Assignment |
|---|---|
| 45.7 | ClCH$_2$CO |
| 118.4 | Ph C-2 and C-5, small J$_{F-C}$ visible |
| 126.2 | Ph C-6, small J$_{F-C}$ visible |
| 131.6 | Ph C-1, small J$_{F-C}$ visible |
| 149.1-156.3 | Ph C-3 and C-4, large J$_{F-C}$ visible |
| 189.3 | ClCH$_2$COPh |

Example 2

Preparation of 2-chloro-1-S-(3,4-difluorophenyl)ethanol

Trimethoxy borane (2.7 g) was added at room temperature to a stirred solution of S-diphenylprolinol (4.7 g) in toluene (128.6 mL). After stirring this mixture for 90 minutes at 40° C. borane dimethylsulfide (22.3 g) was added over 15 minutes maintaining the temperature between 35 and 45° C. This mixture was stirred for 60 minutes at 40° C., then a solution of 2-chloro-1-(3,4-difluorophenyl)ethanone (70.0 g) in toluene (184.1 mL) was dosed over a period of 120 minutes maintaining the temperature between 35 and 45° C. After the completion of the addition, the reaction mixture was stirred for another 60 minutes at 40° C., then cooled to 10° C. Methanol (69.7 g) was added over a period of 20 minutes controlling the gas formation and the temperature to a maximum of 35° C. After the addition the mixture was cooled to 20° C., it was stirred at this temperature for 30 minutes. The obtained solution was then distilled, under reduced pressure at maximum 45° C., until the residual methanol and trimethoxyborane was less than 2 wt %. The obtained solution in toluene was then washed four times with a 10 wt % aqueous HOAc (280.0 mL) at 45 to 55° C. and the obtained water layer back extracted with toluene (140.0 mL). Both organic layers were combined and washed with water (140.0 mL). The resulting organic layer was azeotroped until less than 0.4 wt % water. After correction with toluene, a 33 wt % solution of 2-chloro-1-S-(3,4-difluorophenyl)ethanol was obtained (214.4 g theoretical yield).

The product in solution was characterized by mass spectroscopy (EI):

| M/z | Identification |
|---|---|
| 175.6 | M$^+$ – H$_2$O |
| 143.6 | M$^+$ – CH$_2$Cl |

Example 3

Preparation of ethyl (1R,2R)-trans2-(3,4-difluorophenyl)cyclopropyl carboxylate Sodium hydride (13.4 g) was suspended in toluene (119.9 mL) and the resulting slurry heated to 40° C. Then a solution of triethyl phosphonoacetate (38.4 g) in toluene (60.0 mL) was added over a period of 60 minutes keeping the temperature between 40 and 45° C. When the addition was complete, the reaction mixture was stirred for an additional 60 minutes at 40° C. Then 90.9 g of a 33 wt % solution of 2-chloro-1-S-(3,4-difluorophenyl)ethanol in toluene was added over a period of 35 minutes allowing the temperature to raise to maximum 60° C. Once the addition was complete, the obtained mixture was stirred for an additional 14 hours at 60° C. Then water (155.8 mL) was added and the phases separated at 60° C. The toluene solution containing ethyl (1R,2R)-trans2-(3,4-difluorophenyl)cyclopropyl carboxylate was used as such in the next step.

The product in solution was characterized by mass spectroscopy (EI):

| m/z | Identification |
|---|---|
| 226.3 | M$^{+\cdot}$ |
| 198.3 | M$^{+\cdot}$ – H$_2$C=CH$_2$ |
| 180.4 | M$^{+\cdot}$ – HOCH$_2$CH$_3$ |
| 153.7 | F$_2$PhCH$_2$CH$_2$CH$_2$$^{+\cdot}$ |
| 127.4 | F$_2$Ph$^{+\cdot}$ |

Example 4

Preparation of (1R,2R)-trans2-(3,4-difluorophenyl)cyclopropyl carboxamide

Starting from 2-chloro-1-S-(3,4-difluorophenyl)ethanol (30.9 g), ethyl (1R,2R)-trans2-(3,4-difluorophenyl)cyclopropyl carboxylate was prepared as in example 3. The solvent was distilled and to the resulting oil methanol (109.0 mL), methyl formiate (7.2 g) and 30 wt % sodium methoxide in methanol (11.5 g) were added at room temperature. The mixture was heated to 60° C. in a closed reactor. Then 2 bar NH$_3$-pressure was applied. During a period of 4 hours, the temperature was maintained at 60° C. and the pressure at 2 bar. Then the reactor was cooled to room temperature and vented. The reaction mixture was heated to 60° C. and water (277.2 mL) dosed over 1 hour, the temperature was maintained at 60° C. The resulting solution was cooled to room temperature, then filtered and washed with 1/1 methanol/water (69.3 mL), then with water (49.5 mL) and finally with DiPE (49.5 mL). The resulting crystals were dried at 50° C. in a vacuum oven. After drying, (1R,2R)-trans2-(3,4-difluorophenyl)cyclopropyl carboxamide (22.8 g) was obtained.

Spectral data:

| $^1$H NMR of (1R,2R)-trans 2-(3,4-difluorophenyl) cyclopropyl carboxamide | | |
|---|---|---|
| δ (ppm) | H | Pattern |
| 1.2 | CH (from CH$_2$) | d × d × d |
| 1.6 | CH (from CH$_2$) and CH—CONH$_2$ | d × d × d |
| 2.5 | CH—Ph | d × d × d |
| 5.8 | NH$_2$ | |
| 6.8-7.1 | 3 × Ph—H | M |

| $^{13}$C NMR of (1R,2R)-trans 2-(3,4-difluorophenyl) cyclopropyl carboxamide | |
|---|---|
| δ (ppm) | Assignment |
| 16.7 | CH$_2$ |
| 25.0 | C—CONH$_2$ or C—Ph |
| 26.1 | C—Ph or C—CONH$_2$ |
| 115.3 | Ph C-2, $^2J_{F-C}$: 17.6 Hz |
| 117.6 | Ph C-5, $^2J_{F-C}$: 17.4 Hz |
| 122.7 | Ph C-6, $^3J_{F-C}$: 6.0 Hz and $^4J_{F-C}$: 3.5 |
| 135-155 | Ph C-4 and C-3 |
| 174.3 | CONH$_2$ |

Example 5

Preparation of (1R,2S)-2-(3,4-difluorophenyl)-cyclopropane amine (1R,2R)-trans2-(3,4-difluorophenyl)cyclopropyl carboxamide (25.0 g) and 157.4 g of a 30 wt % solution of NaOH were mixed and heated to 20 to 25° C. A 26 wt % solution of aqueous NaOCl (89.5 g) was dosed over a period of 30 minutes maintaining the temperature below 33° C. Once the addition was finished, the reaction mixture was stirred for an additional 3 hours at 30 to 33° C. The resulting mixture was then heated to 60° C. and stirred at this temperature for an additional 20 minutes.

After cooling to 5° C., the pH of the reaction mixture was corrected with HCl 37 wt % (99.1 g) until a pH of 8.5-9.5 was achieved. iPrOAc (153.3 mL) and MeOH (85.0 mL) were added, followed by water (33.8 mL), after stirring and decantation the phases were separated. The obtained water layer was extracted twice with iPrOAc (75.0 and 55.0 mL respectively). The combined organic phases were diluted until a concentration of 5 wt % was achieved. The obtained solution contains (1R,2S)-2-(3,4-difluorophenyl)-cyclopropane amine (18.0 g in 360.4 g solution).

The product in solution was characterized by mass spectroscopy (APCI).

| m/z | Identification |
|---|---|
| 210.6 | MH$^+$ + CH$_3$CN |
| 169.9 | MH$^+$ |
| 153.2 | MH$^+$ − NH$_3$ |

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, and the like) cited in the present application is incorporated herein by reference in its entirety.

What is claimed is:
1. A process for preparing a compound of formula VII

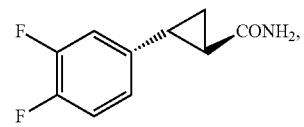

(VII)

comprising:
treating a compound of formula III

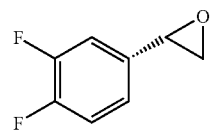

(III)

with a compound of formula 3

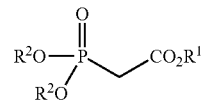

(3)

wherein R$^1$ and R$^2$ are, independently, alkyl, to produce a compound of formula IV

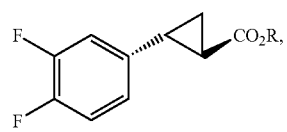

(IV)

wherein R is an alkyl group, and converting the compound of formula IV to a compound of formula VII

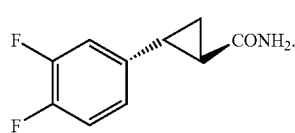
(VII)

2. A process according to claim 1 wherein the compound of formula 3 is triethyl phosphonoacetate.

3. A process according to claim 1 wherein R, $R^1$, and $R^2$ are, independently, selected from methyl, ethyl, n-propyl, iso-propyl, n-butyl, and tert-butyl.

4. A process according to claim 1 wherein the compound of formula IV is treated with ammonia in the presence of a suitable base to produce the compound of formula (VII).

5. A process according to claim 1 further comprising preparing the compound of formula III by treating a compound of formula II

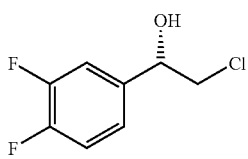
(II)

with a base.

6. A process for preparing a compound of formula VII

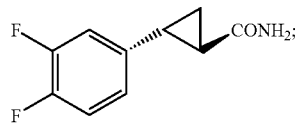
(VII)

comprising:
a) reducing a compound of formula I

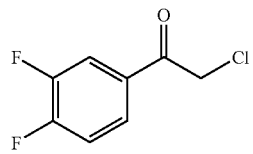
(I)

to give a compound of formula II

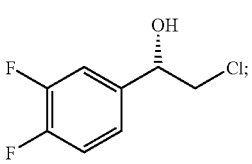
(II)

b) treating the compound of formula II with a base to give a compound of formula III

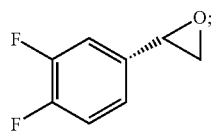
(III)

c) treating the compound of formula III with a compound of formula 3

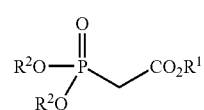
(3)

wherein $R^1$ and $R^2$ are, independently, selected from alkyl, to produce a compound of formula IV

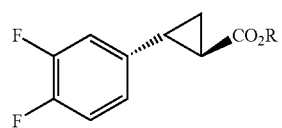
(IV)

wherein R is an alkyl group; and
d) converting the compound of formula IV to a compound of formula VII

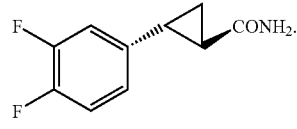
(VII)

7. A process according to claim 6 wherein the compound of formula III is triethyl phosphonoacetate.

8. A process according to claim 6 wherein R, $R^1$ and $R^2$ are, independently, selected from methyl, ethyl, n-propyl, iso-propyl, n-butyl, and tert-butyl.

9. A process according to claim 6 wherein the compound of formula IV is treated with ammonia in the presence of a suitable base to produce the compound of formula (VII).

10. A process for preparing a compound of formula VII

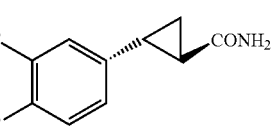
(VII)

comprising:
 a) treating the compound of formula II

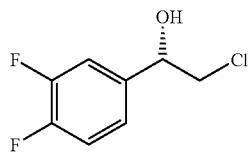
(II)

with a base;
 b) treating the product of a) with a compound of formula 3

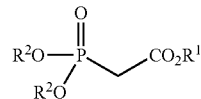
(3)

wherein $R^1$ and $R^2$ are, independently, selected from alkyl to produce a compound of formula IV

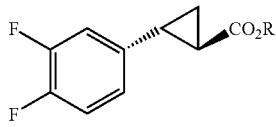
(IV)

wherein R is an alkyl group; and
 c) converting the compound of formula IV to a compound of formula VII

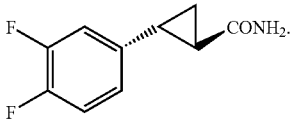
(VII)

11. A process according to claim 10 wherein the base is sodium hydroxide.

12. A process according to claim 10 wherein R, $R^1$ and $R^2$ are, independently, selected from methyl, ethyl, n-propyl, iso-propyl, n-butyl, and tert-butyl.

13. A process according to claim 10 wherein the compound of formula 3 is triethyl phosphonoacetate.

14. A process according to claim 10 wherein the compound of formula IV is treated with ammonia in the presence of a suitable base to produce the compound of formula (VII).

15. A process for preparing a compound of formula VII

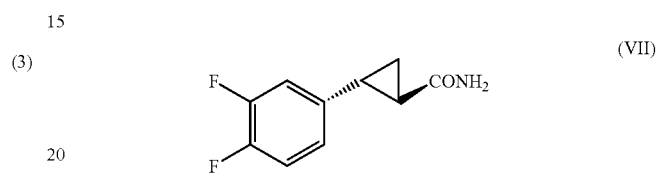
(VII)

comprising treating the compound of formula IV

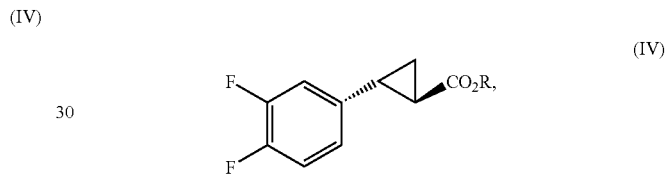
(IV)

wherein R is an alkyl group, with ammonia in the presence of a suitable base.

16. A process according to claim 15 wherein the base is sodium methoxide.

17. A process according to claim 15 wherein the base is potassium methoxide.

* * * * *